United States Patent [19]

Haworth et al.

[11] Patent Number: 5,651,765
[45] Date of Patent: Jul. 29, 1997

[54] BLOOD FILTER WITH CONCENTRIC PLEATS AND METHOD OF USE

[75] Inventors: William S. Haworth, White Bear Lake; Robert W. Olsen, Plymouth; Eric J. Thor, Arden Hills, all of Minn.

[73] Assignee: Avecor Cardiovascular Inc., Plymouth, Minn.

[21] Appl. No.: 429,829

[22] Filed: Apr. 27, 1995

[51] Int. Cl.⁶ .......................... A61M 37/00; B01D 19/00
[52] U.S. Cl. .................. 604/4; 604/5; 210/188; 210/645; 210/493.1; 210/487
[58] Field of Search .................... 604/4, 5, 6; 210/645, 210/646, 647, 315, 188, 435–437, 472, 497.01, 497.03, 321.87, 321.86, 493.1, 487, 512.1

[56] References Cited

U.S. PATENT DOCUMENTS

| | | |
|---|---|---|
| Re. 32,711 | 7/1988 | Dickens et al. . |
| D. 299,269 | 1/1989 | Pierson et al. . |
| 3,105,042 | 9/1963 | Roosa ........................... 210/436 |
| 3,877,903 | 4/1975 | Peterson ....................... 210/493.1 |
| 4,164,468 | 8/1979 | Raible . |
| 4,243,535 | 1/1981 | Behrends et al. ............... 210/315 |
| 4,344,777 | 8/1982 | Siposs . |
| 4,430,223 | 2/1984 | Miyakawa et al. ............. 210/497.01 |
| 4,493,717 | 1/1985 | Berger, Jr. et al. . |
| 4,622,132 | 11/1986 | Chupka ......................... 210/512.1 |
| 4,664,682 | 5/1987 | Monzen . |
| 4,744,902 | 5/1988 | Taki et al. ..................... 210/493.1 |
| 4,919,802 | 4/1990 | Katsura ......................... 210/472 |
| 4,932,987 | 6/1990 | Molina .......................... 210/436 |
| 4,964,984 | 10/1990 | Reeder et al. .................. 210/472 |
| 5,127,900 | 7/1992 | Schickling et al. . |
| 5,258,127 | 11/1993 | Gsell et al. . |
| 5,302,301 | 4/1994 | Stamp et al. .................. 210/512.1 |
| 5,312,479 | 5/1994 | Weinstein et al. ............. 210/436 |

*Primary Examiner*—John G. Weiss
*Assistant Examiner*—Bruce E. Snow
*Attorney, Agent, or Firm*—Popovich & Wiles, P.A.

[57] ABSTRACT

An arterial line blood filter for use in extracorporeal blood circuits during heart bypass surgery. The blood filter includes a housing having a cap portion, a base portion and a generally cylindrical wall portion. A filter element is disposed within the housing and divides the housing into an inlet chamber in flow communication with a blood inlet and an outlet chamber in flow communication with a blood outlet. The filter element may include a plurality of concentric annular pleats, the length of which may be substantially equal to the length of the wall portion, the pleats being supported by a support element. In another embodiment the inner surface of the cap defines an inwardly spiral blood flow path which slopes upward and provides an effective means of distributing blood over the filter element.

18 Claims, 4 Drawing Sheets

BLOOD FILTER WITH CONCENTRIC PLEATS AND METHOD OF USE

FIELD OF THE INVENTION

This invention relates to blood filters used in extra corporeal blood circuits. More particularly, the invention is directed to an arterial line blood filter used during heart bypass surgery to filter solid particulate and gaseous emboli from blood that has been oxygenated and is being returned to the patient.

BACKGROUND OF THE INVENTION

During open heart surgery the blood of the patient is bypassed to an extra corporeal blood circuit. The circuit commonly includes a support system which supplies the pumping function of the heart and the oxygenation function of the lungs. This effectively isolates the heart and lungs enabling the surgeon to make the necessary repairs to the heart and/or lungs. Both venous blood and cardiotomy blood from the surgical site may be removed and circulated through the extra corporeal circuit.

Blood filters are typically included both upstream and downstream from the oxygenator which may incorporate a heat exchanger. Upstream blood filters include venous and cardiotomy filters through which the blood may be filtered prior to entering the oxygenator and which are used to remove particulate, especially from the surgical site, and bubbles from the blood. Although these upstream filters are effective it is possible that some emboli may pass through or be generated in the oxygenator and/or heat exchanger. These emboli may be in suspension in the oxygenated blood which is to be returned to the patient. The embolic material can be either particulate, such as platelet or white cell aggregates, or gaseous, such as small or large gas bubbles. Therefore, an arterial line filter which is located downstream of the oxygenator is critically important in trapping and removing any remaining emboli before the blood is provided to the patient.

A typical conventional arterial blood filter is illustrated in FIG. 1. The filter includes a blood inlet located at the top of the filter. In this case the inlet is located in a tangential position. A radially pleated tubular filter is disposed within a cylindrical housing and is covered by a cortically shaped cap. The arrow shows the path of blood as it flows through the filter. After entering through the tangential inlet the blood travels in a circular path over and around the cap and down between the outer wall of the housing and the pleated filter. The blood eventually passes through the filter and is discharged through a blood outlet at the bottom of the device. A gas port is located at the top of the device through which air bubbles or gaseous emboli may be vented.

Although conventional arterial blood filters are effective in achieving significant reductions in emboli they share several common problems. First, they include significant horizontal surface area in the blood flow path. Bubbles tend to attach themselves to these horizontal surfaces increasing the difficulty of priming and, therefore, making the filters more difficult to use. Second in many radially pleated designs, blood flows down through a small annular gap between the filter element and the housing. At a given flow rate, the smaller this area is, the higher is the downward blood velocity. Higher blood velocities entrain smaller air bubbles which subsequently get trapped in the filter element or get broken up into smaller bubbles and pass through the filter. It would be desirable to have as large an area as possible available for downward flow to reduce downward entrainment of small air bubbles. Third, in many conventional arterial filters the priming volume is not utilized efficiently. Generally, the bigger the prime volume of a filter, the longer the time available for air bubbles to separate because of their buoyancy. However, there is also a desire to minimize prime volume in order to avoid unnecessary use of blood and blood products. The best balance is achieved by ensuring that as much of the prime volume as possible is upstream of the filter screen, because this is the region in which air can separate by buoyancy. Fourth, in most radially pleated designs the frontal area for flow downstream of the filter element is substantially reduced from the frontal area upstream of the filter element. Thus the blood velocity significantly increases after it passes through the filter element in conventional designs. This higher velocity tends to entrain bubbles which have passed through the filter element and carries them toward the outlet port where the bubbles may be conducted to the patent. It is desirable to maintain the frontal area for flow adjacent to the downstream side of the filter element as large as possible, or at least as close as feasible to the frontal area upstream of the filter element. Fifth, radially pleated designs incorporate a shallow annular or disk shaped potting cup to mount the top and bottom of the filter element. The filter element end is immersed in the liquid potting compound and held in position until the compound solidifies. Since the cup is rarely completely filled with the potting compound, a concave surface is formed by the potting compound and the lip of the cup. Concave surfaces can also be created by the liquid potting compound wicking up the filter element while the compound is hardening from a liquid to a solid. In use bubbles can become trapped under the concave surface of the upper potting cup. When the filter is inverted during priming to remove these trapped bubbles they can rise and be trapped under the concave surface of the bottom potting cup which is now on top. This bubble trapping complicates priming the filter. It is desirable to create a design which does not require potting either the top or bottom of the filter element. Thus, it would be desirable to provide an arterial blood filter which not only has efficient emboli removal capabilities but is also easier to prime and provides more opportunity for buoyancy separation of air than do conventional filters.

SUMMARY OF THE INVENTION

In accordance with the present invention there is disclosed an arterial blood filter combining efficient filtering characteristics, large frontal area for flow, and a high prime volume upstream of the screen. The blood filter is easy to prime and overcomes the problems which exist in prior art devices. The arterial blood filter comprises a housing having a cap portion, a base portion and a generally cylindrical wall portion. In one embodiment the inner surface of the cap defines an inwardly spiral blood flow path which slopes upward. A blood inlet is in flow communication with the inwardly spiral blood flow path. A filter element is disposed within the housing and divides the housing into an inlet chamber in flow communication with the blood inlet and an outlet chamber in flow communication with a blood outlet. The filter element may include a plurality of concentric annular pleats, the length of which may be substantially equal to the length of the wall portion between the cap portion and the base portion. The blood filter includes a support element having a base member and a plurality of concentric annular members nested within and supporting the annular pleats of the filter element. A gas vent is provided in gas flow communication with the inlet chamber.

The blood filter may include a volume displacing element disposed within an innermost annular pleat of the support element. The volume displacing element may be an extension of the cap portion. The annular members of the support element may be generally cylindrical and have an inner cylindrical surface, an outer cylindrical surface and an axis which coincides with the axis of the cylindrical wall portion. At least one of the inner cylindrical surface and the outer cylindrical surface of the annular members may be fibbed to provide spacing between the filter element and the support element. Further, each annular member may comprise a plurality of flat facets such that the annular members are in the shape of polyhedrons. The ends of the annular elements opposite the base member may be notched to allow more efficient blood flow.

In another embodiment the invention is a blood filter comprising a cap which defines an inwardly spiral blood flow path which slopes upward. The blood filter further includes a tubular wall section, and a base which, together with the cap, define a blood filtering chamber. A blood inlet is provided in flow communication with the inwardly spiral blood flow path. A filter element disposed within the housing divides the housing into an inlet chamber in flow communication with the blood inlet and an outlet chamber in flow communication with a blood outlet. The filter element is provided with a plurality of concentric annular pleats, each pleat having a length equal to approximately the length of the tubular wall section. A volume displacing element integral with the cap extends towards the filter element such that it is disposed within an innermost annular pleat of the filter element. A support element having a base member and a plurality of concentric annular members extends from the base member and terminates at an edge which nests within and supports the annular pleats of the filter element. The blood filter has a gas vent in flow communication with the inlet chamber.

The annular members of the support element may be generally cylindrical and have an inner cylindrical surface, an outer cylindrical surface and an axis which coincides with the axis of the cylindrical wall portion. At least one of the inner cylindrical surface and the outer cylindrical surface of the annular members are ribbed to provide spacing between the filter element and the support element. Each annular member may comprise a plurality of flat facets such that the annular members are in the shape of polyhedrons. The supporting edges of the annular elements may be notched to provide more efficient blood flow.

In a further embodiment the invention comprises a method for filtering blood. The method comprises providing a blood filter having a housing which defines a blood filtering chamber. The chamber is divided into a blood inlet chamber and a blood outlet chamber by a filter element. In one aspect of the invention the filter element may include concentric pleats. The concentric pleats are supported in the chamber by a support element having a plurality of concentric annular members nested in the concentric pleats of the filter element. The method includes circulating blood through a blood inlet into the inlet chamber. The blood flow may be directed in an inwardly spiral and upward blood flow path such that the blood is distributed over and flows through the concentric annular pleats of the filter element. Particles and bubbles are filtered from the blood as it passes through the filter element to the outlet chamber. The blood is discharged from the outlet chamber through a blood outlet. The method may further include removing air from the inlet chamber through a vent provided at a top portion of the inlet chamber.

BRIEF DESCRIPTION OF THE DRAWINGS

The foregoing and other aspects of the present invention will be best appreciated with reference to the detailed description of the invention, which follows, when read in conjunction with the accompanying drawings wherein.

DETAILED DESCRIPTION OF THE INVENTION

Construction of the Blood Filter

Figure 1:
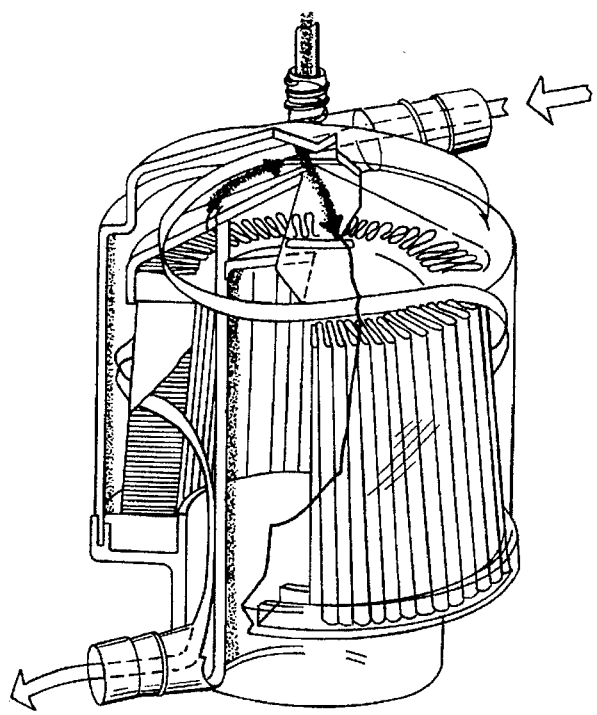
FIG. 1 is a partially cut away perspective view of a typical prior art arterial blood filter.
Figure 2:
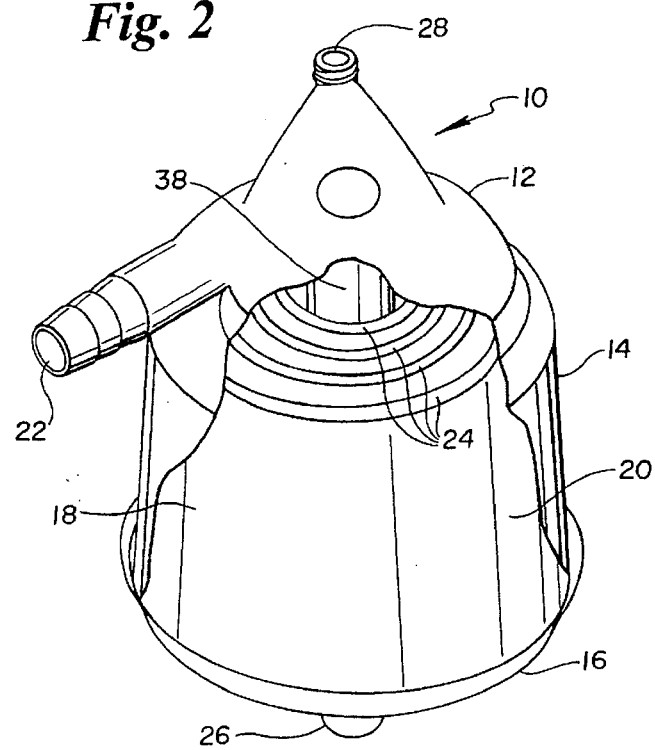
FIG. 2 is a perspective view of an arterial blood filter according to the present invention with a portion of the housing broken away to show the concentric pleats of the filter element.
Figure 3:
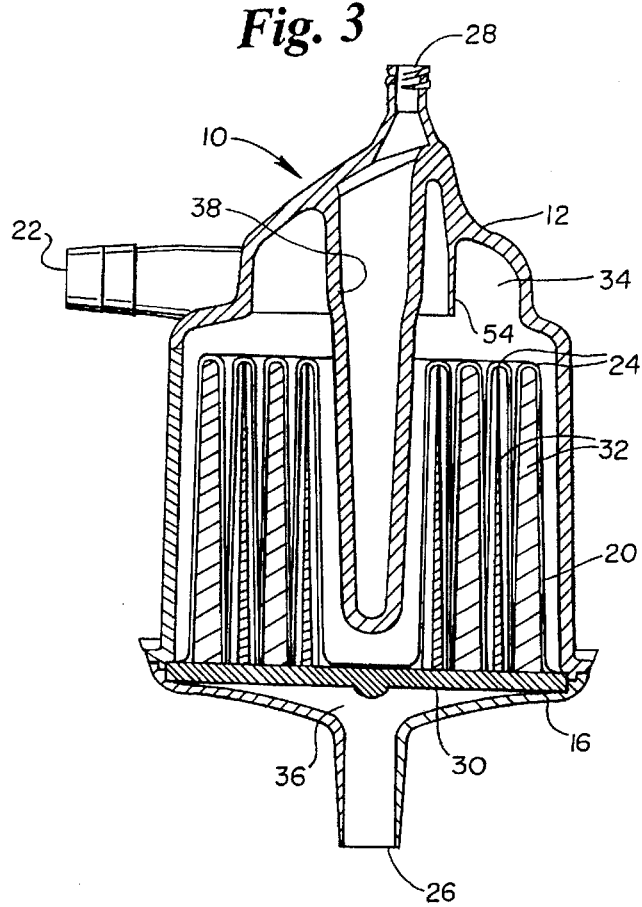
FIG. 3 is a cross-sectional side view of the arterial blood filter of FIG. 2.

FIGS. 2 and 3 are perspective and sectional views of an arterial blood filter 10 in accordance with the present invention. Blood filter 10 has a housing which includes a cap portion 12, a tubular wall portion 14 and a base portion 16. The housing encloses a blood filtering chamber 18 which contains a filter element 20 having a plurality of concentric pleats 24. As will be discussed in more detail with respect to FIGS. 3 and 6–8, filter element 20 is supported by a support element, not shown in FIG. 2. Cap portion 12, wall portion 14 and base portion 16 may be formed from separate pieces and bonded together in a conventional manner. Alternatively, wall portion 14 may be constructed as an integral piece with either cap 12 or base portion 16. In the preferred embodiment shown in FIGS. 2 and 3 the cap portion 12 is integral with wall portion 14. Preferably, the housing is made of a transparent medical grade material so that the user is able to observe the flow of blood through the device.

A blood inlet 22 is located at an upper position on the housing to enable blood to be circulated through the blood filtering chamber 18. Blood inlet 22 may be connected to a line from an oxygenator (not shown) for receiving oxygenated blood. In the embodiment shown in FIG. 2 the blood inlet is formed as an integral portion of cap 12. Inlet 22 is constructed such that when the filter is placed in its upright position with the cap at the top, as shown in FIG. 2, the blood enters horizontally at one side of the blood filter. After the blood enters the blood filter it is directed by the cap in an inwardly spiral path as will be discussed in more detail with respect to FIGS. 4 and 5. A blood outlet 26 is located at the bottom of the housing in the base portion 16. The outlet 26 is connected to a patient return line (not shown) for providing oxygenated blood back to the patient. A gas vent 28 is located at or near the top of cap portion 12. Vent 28 provides a means of venting from the blood filter gaseous emboli which rises to the top of cap portion 12. The vent 28 is located at the highest point of cap 12.

FIG. 3 is a cross-sectional side view of the arterial blood filter of FIG. 2. A support element 30 is positioned within the housing to provide support for the concentric pleats 24 of filter element 20. Generally, any manner of support which results in stabilizing the annular pleats may be used. Preferably, support element 30 includes a plurality of concentric annular members 32, each larger than the previous, which nest within the concentric pleats 24. Each annular member is a generally cylindrical tubular section. As shown in FIG. 3, the pleats are generally concentric to the longitudinal axis of the blood filter and spaced apart from the surrounding wall portion and each other to leave sufficient space for blood to flow down and through the filter member. Inside of the innermost concentric pleat is a volume displacer 38. Volume displacer 38 is a closed end tube which extends from the cap portion 12 towards the base portion 16. It may be formed as an integral part of cap portion 12, as shown, or it may be a separate piece which is bonded to the cap portion. Although volume displacer 38 is optional, it's use is desirable since it serves the important function of lowering the priming volume of the blood filter.

The Concentric Pleated Filter Element

The concentric pleats of the filter element are formed from a conventional filter screen fabric. The filter screen fabric is cut and one or more seams bonded so the resulting shape is a hollow cone. The axis of the pattern may be cut on the bias of the screen threads. A bias cut allows the screen to conform better to the desired shape without forming wrinkles, creases, or bulges. The cone is formed into concentric pleats by shaping the screen over the annular members of the support element using cylindrical forming sleeves.

The filter element 20 is bonded along the outer periphery of the support element 30. The filter screen is also bonded to each spoke of the filter support element to prevent the screen cone from inverting if flow through the filter is retrograde. Support element 30 is in turn bonded to the base portion 16 such that when the blood filter is assembled filter element 20 divides blood filtering chamber 18 into a blood inlet chamber 34 and a blood outlet chamber 36.

With continued reference to FIG. 3, it will be appreciated that the length of the annular members 32 of the support element 30 is approximately the same as the length of the wall portion 14 between the cap portion 12 and the base portion 16. Thus, the pleated filter element formed over the support element approximately fills the blood filtering chamber between the cap portion and base portion of the housing. This configuration is desirable in order to maximize the amount of surface area of the filter element which is exposed to blood flow. Additionally, the support element 30 including annular members 32 provide the added benefit of displacing additional volume resulting in the further lowering of the priming volume of the blood filter on the downstream side of the filter screen.

The number of annular pleats (and consequently the number of annular members) is selected to maximize the surface area of the filter element which is exposed to blood flow while at the same time leaving enough space between adjacent pleats, the wall portion and the volume displacer so that efficient blood flow may be maintained. In the preferred embodiment shown four pleats are used. It will be appreciated, however, by those of skill in the art with knowledge of the present invention that fewer or more pleats may be used within the scope of the invention.

The Support Element

Figure 6:
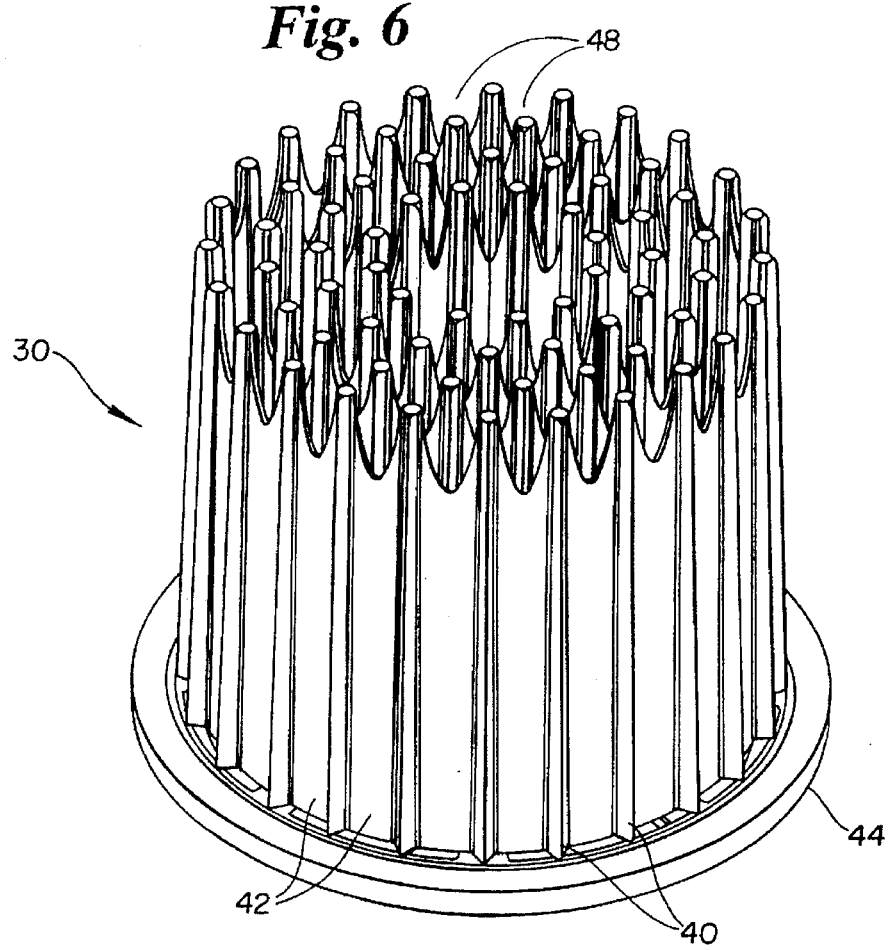
FIG. 6 is a perspective view of the support element utilized in the arterial blood filter of FIG. 2.
Figure 7:
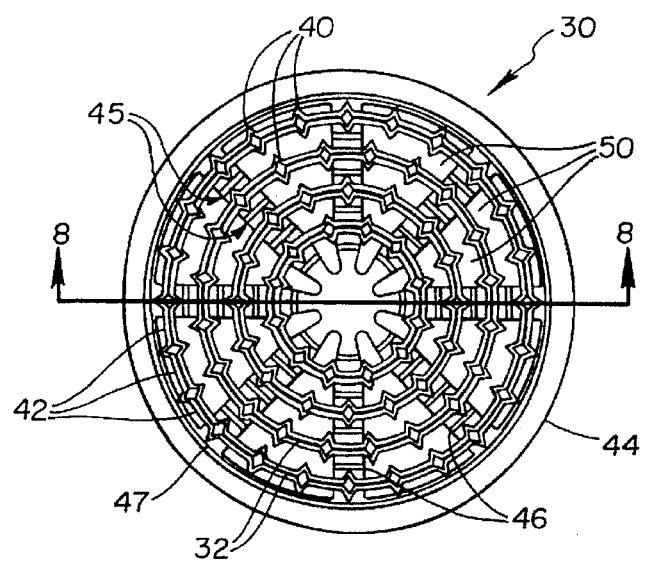
FIG. 7 is a top view of the support element of FIG. 6.
Figure 8:
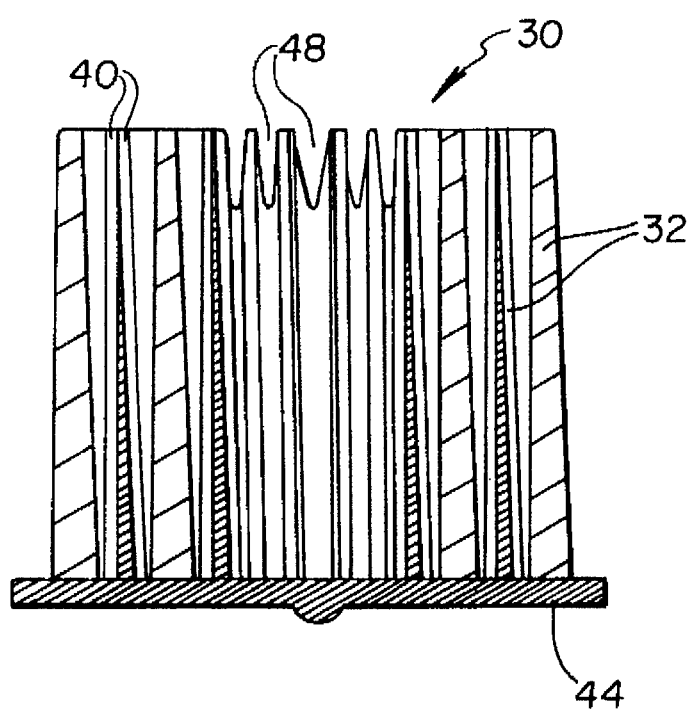
FIG. 8 is a sectional view of the support element taken along line 8—8 of FIG. 7.

Support element 30 is shown in more detail in FIGS. 6–8. FIG. 6 is a perspective view of the support element showing the concentric ringed configuration of the annular members. FIG. 7 is a top view of the support element. FIG. 8 is a cross-sectional view of the support element taken along line 8—8 of FIG. 7. Support element 30 includes a base ting 44. Base ting 44 provides support for a network of spokes 46 from which the annular members 32 project. Each of the components including base ting 44, spokes 46 and annular members 32 may be made separately and then bonded together in a conventional manner to form support element 30. Preferably, support element 30 is molded from a medical grade plastic as a single integral piece which is bonded in a conventional manner to base portion 16. Alternatively, support element 30 may be formed as an integral portion of base portion 16.

In order to hold the filter element off of the surface of the annular members ribs 40 may be provided on the inner and/or outer cylindrical surfaces of one or more of the annular members. In the preferred embodiment shown in the figures the ribs are diamond shaped in cross-section, are generally parallel to the longitudinal axis of the blood filter and protrude from both the inner and outer cylindrical surfaces of each annular member. The number of ribs and their orientation with respect to the surface of the annular members may be varied. For example, the ribs may project from either the inner cylindrical surface or the outer cylindrical surface or both, as shown. Likewise, the ribs need not be parallel to the axis of the blood filter. Preferably, the ribs on the outer surface of one cylindrical annular member do not line up with the ribs on the inner surface of the adjacent annular member. This facilitates the molding process since it allows the metal in the mold to be thicker at the base of the support element where the ribs are in closest proximity. This enables the mold to be made stronger and more durable. It also conducts heat more rapidly so it cools more quickly after the plastic is injected during the molding process. The ribs provide a path between the filter element and the cylindrical surface of the annular members for blood which has passed through the filter element to flow from the outlet chamber to the blood outlet.

The cylinders which form the annular members may comprise flat planar facets 42 between ribs 40 such that the resultant shape is a polyhedron. Such a configuration maximizes the gap between the filter element and the inner and outer surfaces of the facets. This further ensures that the blood flow path between the filter element and the surfaces of the facets is adequate. In order to minimize the surface area of the filter element which is blocked off by contact with the upper edge of the annular members the top edge of the facets 42 may be provided with notches 48. Notches 48 allow blood to flow through the filter element at the top of the pleats in areas that would be blocked in the absence of the notches. After passing through the filter element the blood flows in a downward direction through outlet slots 50 formed between spokes 46 and annular members 32 and out of the blood filter through blood outlet 26.

Inlet Blood Flow Path

Figure 4:
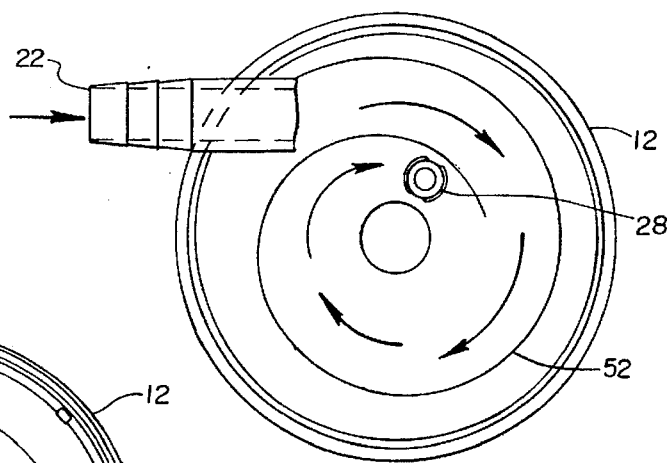
FIG. 4 is a top view of the cap of the arterial blood filter of FIG. 2.
Figure 5:
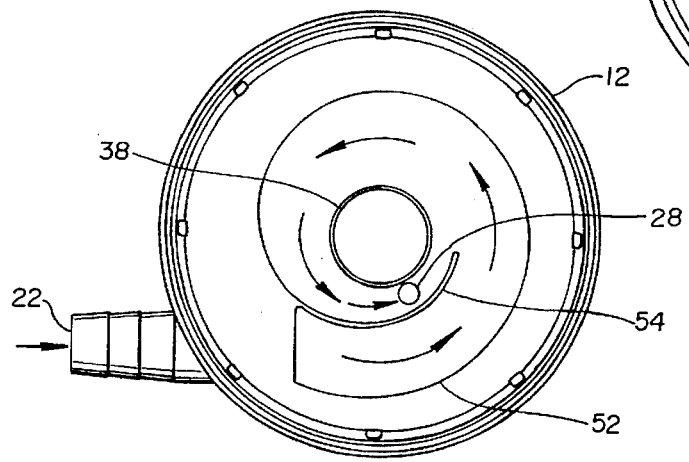
FIG. 5 is a bottom view of the cap of FIG. 4.

The path followed by blood from the inlet 22 is best shown in FIGS. 4 and 5. FIGS. 4 and 5 are top and bottom views of cap portion 12, respectively. As illustrated by the arrows, the blood is directed to flow in an inward spiral by the inner surface 52 of cap portion 12. The tightness of the spiral increases along the flow path as the blood is directed around the volume displacer 38 inwardly towards the center of the blood filter. A flow director 54 is provided to separate blood which has circled around the blood filter from blood just entering through the blood inlet. Such interaction could reduce the cross sectional area available for flow of the inlet blood. This would increase the blood velocity in this region, which can increase the pressure losses in the inlet, increase damage to the blood and disrupt the even supply of blood over the pleats of the filter element. In addition, the flow director prevents bubbles which are rising to the vent port from mixing with blood entering from the inlet which is traveling at a high velocity. This prevents the high velocity inlet blood flow from breaking up bubbles rising to the vent port and from entraining those bubbles.

Operation of the Blood Filter

In use, blood enters the inlet chamber through blood inlet 22. The blood flow is directed by the shape of inner surface 52 of the cap portion 12 in an inward spiral. Since the cross-sectional flow area in the inlet chamber is greater than the cross-sectional area of the inlet tubing, the inlet chamber acts as a diffuser and decreases the velocity of the blood. As the blood continues its flow at a decreased velocity around the cap portion of the blood filter some blood begins to flow downward into the concentric annular pleats. Because the blood velocity is decreased and the blood is directed inwardly, there tends to be an even distribution of blood over the pleats.

As the blood follows its path through the filter gaseous emboli rise to the top surface of the cap portion which is sloped upward and toward the vent. The inward flow path of blood carries the emboli around the spiral to the elevated region of the vent where they collect for venting. The elevated region of the vent is above the blood flow path so that the area is protected from high velocity blood flows which would flush the gaseous emboli out of the elevated vent region.

As the blood is distributed over the concentric pleats it passes through the filter element into the output chamber. The blood is then directed by the cylindrical annular members downward and through the output slots. From there it exits the blood filter through the blood outlet where it may be delivered to a patient through a patient return line.

From the foregoing detailed description of specific embodiments of the invention, it should be apparent that an improved arterial blood filter has been disclosed. Although particular embodiments of the invention have been disclosed herein in detail, this has been done for the purpose of illustration only, and is not intended to be limiting with respect to the scope of the appended claims, which follow. In particular, it is contemplated by the inventors that various substitutions, alterations and modifications may be made to the embodiments of the invention without departing from the spirit and scope of the invention as defined by the claims.

We claim:

1. A blood filter comprising:
    a housing having a cap portion, a base portion and a generally cylindrical wall portion;
    a blood inlet;
    a filter element disposed within the housing and dividing the housing into an inlet chamber in flow communication with the blood inlet and an outlet chamber, the filter element having a plurality of concentric annular pleats;
    a support element fixedly connected to the housing, the support element having a plurality of concentric annular members nested within the annular pleats of the filter element;
    a blood outlet in flow communication with the outlet chamber;
    a gas vent in gas flow communication with the inlet chamber; and
    a volume displacing element disposed within an innermost annular pleat of the filter element, the volume displacing element comprising an extension of the cap portion.

2. A blood filter comprising:
    a housing having a cap portion, a base portion and a generally cylindrical wall portion;
    a blood inlet;
    a filter element disposed within the housing and dividing the housing into an inlet chamber in flow communication with the blood inlet and an outlet chamber, the filter element having a plurality of concentric annular pleats;
    a support element fixedly connected to the housing, the support element having a plurality of concentric annular members nested within the annular pleats of the filter element, and the support element also having a base member from which the annular members extend;
    a blood outlet in flow communication with the outlet chamber; and
    a gas vent in gas flow communication with the inlet chamber.

3. The blood filter of claim 2 wherein the annular members are generally cylindrical and have an inner cylindrical surface, an outer cylindrical surface and an axis which coincides with the axis of the cylindrical wall portion.

4. The blood filter of claim 3 wherein at least one of the inner cylindrical surface and the outer cylindrical surface of the annular members are ribbed to provide spacing between the filter element and the support element.

5. The blood filter of claim 3 wherein each annular member comprises a plurality of flat facets such that the annular members are in the shape of polyhedrons.

6. The blood filter of claim 4 wherein the annular elements extend from the base portion to a notched end portion.

7. A blood filter comprising:
    a housing having a cap portion, a base, a generally cylindrical wall portion and a blood flow separation portion, the cap portion defining a blood flow path which spirals inwardly;
    a blood inlet in flow communication with the inwardly spiral blood flow path, the blood flow separation portion being positioned as a barrier between blood entering through the blood inlet and blood which has previously entered the filter and is flowing along the inwardly spiral blood flow path;
    a filter element disposed within the housing and dividing the housing into an inlet chamber in flow communication with the blood inlet and an outlet chamber, and the filter element having a plurality of concentric pleats;
    a blood outlet in flow communication with the outlet chamber;
    a gas vent in gas flow communication with the inlet chamber; and
    a support element having a plurality of annular members nested within and supporting the annular pleats of the support element.

8. The blood filter of claim 7 wherein the support element includes a base member from which the annular members extend.

9. The blood filter of claim 8 wherein the annular members are generally cylindrical and have an inner cylindrical surface, an outer cylindrical surface and an axis which coincides with the axis of the cylindrical wall portion.

10. The blood filter of claim 9 wherein at least one of the inner cylindrical surface and the outer cylindrical surface of the annular members are ribbed to provide spacing between the filter element and the support element.

11. The blood filter of claim 9 wherein each annular member comprises a plurality of flat facets such that the annular members are in the shape of polyhedrons.

12. The blood filter of claim 10 wherein the annular elements extend from the base portion to a notched end portion.

13. A blood filter comprising:

a housing having a cap portion, a base, a generally cylindrical wall portion and a blood flow separation portion, the cap portion defining a blood flow path which spirals inwardly;

a blood inlet in flow communication with the inwardly spiral blood flow path, the blood flow separation portion being positioned as a barrier between blood entering through the blood inlet and blood which has previously entered the filter and is flowing along the inwardly spiral blood flow path;

a filter element disposed within the housing and dividing the housing into an inlet chamber in flow communication with the blood inlet and an outlet chamber;

a blood outlet in flow communication with the outlet chamber;

a gas vent in gas flow communication with the inlet chamber; and a volume displacing element disposed within an innermost annular pleat of the support element, and comprising an extension of the cap portion.

14. A blood filter comprising:

a cap defining an inwardly spiral blood flow path;

a tubular wall;

a base, wherein the cap, tubular wall and base together define a blood filtering chamber;

a blood inlet in flow communication with the inwardly spiral blood flow path;

a filter element disposed within the housing and dividing the housing into an inlet chamber in flow communication with the blood inlet and an outlet chamber, the filter element having a plurality of concentric annular pleats, each pleat having a length equal to approximately the length of the tubular wall;

a volume displacing element connected to the cap and extending towards the filter element such that it is disposed within an innermost annular pleat of the support element;

a support element fixedly connected to the base, the support element having a base member and a plurality of concentric annular members extending from the base member and terminating at an edge which nests within and supports the annular pleats of the filter element;

a blood outlet in flow communication with the outlet chamber; and a gas vent in gas flow communication with the inlet chamber.

15. The blood filter of claim 14 wherein the annular members are generally cylindrical and have an inner cylindrical surface, an outer cylindrical surface and an axis which coincides with the axis of the cylindrical wall portion.

16. The blood filter of claim 15 wherein at least one of the inner cylindrical surface and the outer cylindrical surface of the annular members are ribbed to provide spacing between the filter element and the support element.

17. The blood filter of claim 15 wherein each annular member comprises a plurality of flat facets such that the annular members are in the shape of polyhedrons.

18. The blood filter of claim 14 wherein the supporting edges of the annular elements are notched.

* * * * *